(12) United States Patent
Kumagai et al.

(10) Patent No.: US 9,139,650 B2
(45) Date of Patent: Sep. 22, 2015

(54) FRAGMENT OF HUMANIZED ANTI-EGFR ANTIBODY SUBSTITUTED-LYSINE VARIABLE FRAGMENT AND USE THEREOF

(75) Inventors: Izumi Kumagai, Sendai (JP); Takeshi Nakanishi, Sendai (JP); Hideaki Sanada, Sendai (JP); Ryutaro Asano, Sendai (JP); Mitsuo Umetsu, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 0 days.

(21) Appl. No.: 13/816,420

(22) PCT Filed: Jul. 16, 2011

(86) PCT No.: PCT/JP2011/066281
§ 371 (c)(1),
(2), (4) Date: Jun. 25, 2013

(87) PCT Pub. No.: WO2012/020622
PCT Pub. Date: Feb. 16, 2012

(65) Prior Publication Data
US 2013/0274446 A1    Oct. 17, 2013

(30) Foreign Application Priority Data
Aug. 12, 2010    (JP) .................................. 2010-180693

(51) Int. Cl.
*A61K 39/395*    (2006.01)
*C07K 16/28*    (2006.01)

(52) U.S. Cl.
CPC .......... *C07K 16/2863* (2013.01); *C07K 2317/24* (2013.01); *C07K 2317/622* (2013.01); *C07K 2317/626* (2013.01)

(58) Field of Classification Search
CPC ............ A61K 39/0011; C07K 16/2863; C07K 2317/622; C07K 2317/626
See application file for complete search history.

(56) References Cited

U.S. PATENT DOCUMENTS

| | | | | |
|---|---|---|---|---|
| 4,904,584 | A | * | 2/1990 | Shaw ........................... 435/69.4 |
| 4,943,533 | A | * | 7/1990 | Mendelsohn et al. ... 530/388.22 |
| 2006/0210564 | A1 | | 9/2006 | Kumagai et al. |
| 2008/0242607 | A1 | | 10/2008 | DeFrees |
| 2008/0305116 | A1 | | 12/2008 | Van Vlijmen et al. |
| 2009/0202532 | A1 | | 8/2009 | Kumagai et al. |
| 2013/0131320 | A1 | | 5/2013 | Kumagai et al. |

FOREIGN PATENT DOCUMENTS

| | | |
|---|---|---|
| JP | 2004-242638 A | 9/2004 |
| JP | 2008-511290 A | 4/2008 |
| JP | 2009-544327 A | 12/2009 |
| JP | 2010-119303 A | 6/2010 |
| WO | WO 99/67291 A2 | 12/1999 |
| WO | WO 2007/108152 A1 | 9/2007 |
| WO | WO 2011/062112 A1 | 5/2011 |

OTHER PUBLICATIONS

Onda et al. (Bioconjugate Chem., 14: 480-487, 2003).*
Asano et al. Highly Effective Recombinant Format of a Humanized IgG-like Bispecific Antibody for Cancer Immunotherapy with Retargeting of Lymphocytes to Tumor Cells, Journal of Biological Chemistry, vol. 282, No. 38, Sep. 21, 2007, pp. 27659-27665, XP55043823.
Asano et al. "Preferential heterodimerization of a bispecific diabody based on a humanized anti-EGFR antibody 528", Protein Engineering, Design & Selection, vol. 21, No. 10, 2008, published online Jul. 11, 2008, pp. 597-603, XP55043822.
Benhar et al., "Mutations of Two Lysine Residues in the CDR Loops of a Recombinant Immunotoxin That Reduce Its Sensitivity to Chemical Derivatization", Bioconjugate Chem. vol. 5, Jul. 1, 1994, pp. 321-326, XP000564453.
Debinski et al., "An Immunotoxin with Increased Activity and Homogeneity Produced by Reducing the Number of Lysine Residues in Recombinant Pseudomonas Exotoxin", Bioconjugate Chemistry, vol. 5, No. 1, Jan./Feb. 1994, pp. 40-46, XP000430384.
Extended European Search Report dated Apr. 24, 2014 for Application No. 11816288.2.
Kumagai et al. "Integration of PEGylation and refolding for renaturation of recombinant proteins from insoluble aggregates produced in bacteria-Application to a single-chain Fv fragment", Journal of Bioscience and Bioengineering, vol. 109, No. 5, May 5, 2010, pp. 447-452, XP-002722553.
Kortt et al., "Dimeric and trimeric antibodies: high avidity scFvs for cancer targeting", Biomolecular Engineering, vol. 18, 2001, pp. 95-108.
Onda et al., "Mutants of Immunotoxin Anti-Tac(dsFv)-PE38 with Variable Number of Lysine Residues as Candidates for Site-Specific Chemical Modification. 1. Properties of Mutant Molecules", Bioconjugate Chem., vol. 14, 2003, pp. 480-487.
Yamamoto et al., "Site-specific PEGylation of a lysine-deficient TNF-α with full bioactivity", Nature Biotechnology, vol. 21, May 2003, pp. 546-552.

* cited by examiner

*Primary Examiner* — Brad Duffy
*Assistant Examiner* — Nelson B Moseley, II
(74) *Attorney, Agent, or Firm* — Birch, Stewart, Kolasch & Birch, LLP.

(57) ABSTRACT

The purpose of the present invention is to provide fragments of humanized anti-EGFR antibody substituted-lysine light-chain or heavy-chain variable regions, and single-chain antibodies, etc, comprising the same, having sufficient binding activity (affinity) with target cells, and having the ability to undergo various site-specific and uniform chemical modifications. The present invention pertains to a humanized variable region on the light-chain or heavy-chain of antibody 528 against human epidermal cell growth factor receptor 1 (Her-1), said variable region comprising the amino acid sequence represented by SEQ ID NO: 2 or SEQ ID NO: 4, wherein fragments of humanized anti-EGFR antibody lysine-substituted light-chain variable regions are formed by substituting a different amino acid for all of the lysine residues, or all of the lysine residues except for the lysine residue(s) of one specified moiety.

13 Claims, 6 Drawing Sheets
(6 of 6 Drawing Sheet(s) Filed in Color)

Dimer of HK(LK) C0

Ca. 40Å
Ca. 12Å

Dimer of HK(LK) C6

Ca. 27Å

Antibody is added to A431 and growth-inhibition is observed

FRAGMENT OF HUMANIZED ANTI-EGFR ANTIBODY SUBSTITUTED-LYSINE VARIABLE FRAGMENT AND USE THEREOF

FIELD OF THE INVENTION

The present invention is related to a lysine-substituted (or lysine-replaced) humanized variable region fragment of an anti-EGFR antibody and its use, wherein all of the lysine residues, or all of the lysine residues except for one lysine residue at an optionally-selected particular site in the humanized variable region of a light- or heavy- chain of the anti-human epithelial cell growth factor (EGF) receptor 1 (Her1) (EGFR) antibody 528 is replaced by other suitable amino acids.

BACKGROUND OF THE INVENTION

Recently, immunotherapy has been used as a safe therapy for the treatment of cancer, rheumatoid, etc. In the immunotherapy of cancer, an antibody showing a cytotoxic activity specifically upon cancer cells is used. While it is recognized that an antibody drug comprising such antibody will show high and safe therapeutic effects with little side effects, it has a problem that it would cost much since said drug needs to be produced by using established animal cells.

As a result, it has been a worldwide trend to produce a low molecular-weight antibody such as a single-chain antibody (scFV) that contains VH and VL of a certain antibody in a single-chain polypeptide. Such low molecular-weight antibody can be economically produced by E. coli. However, it is concerned that its half-life in a body will be decreased due to its low molecular weight, reducing the period of effecting medical benefits. Also, it is a problem that affinity of such low molecular-weight antibody with monovalence is lower than that of a full antibody such as IgG with polyvalence for a target antigen. Furthermore, as a main mechanism of an action of the antibody drug is considered to be an antibody dependent cytotoxic activity (ADCC) via Fc region, it is concerned that the ADCC of the scFv that has no Fc region would be low. Non-Patent Document 1 may be referred to with respect to the scFv.

Accordingly, a bispecific antibody with a low molecular weight has been developed, which can cross-link between cancer cells and immune cells. Only one of such bispecific antibody with a low molecular weight, called "BiTE", which consists of two fragments of scFv linked with each other in tandem, has been now brought into a clinical trial (Science 2008 Aug. 15: 321 (5891): 974-7). However, as the BiTE is produced by using animal cells, its production cost and yield have become problematic. Furthermore, it was reported that it was difficult to prepare the tandem scFv-type bispecific antibody with a low molecular weight such as BiTE from soluble fraction of E. coli (J Mol Biol, 2003 330(1)99-111).

Among antibodies with multiple specificities, an antibody with bispecificity (Bispecific Antibody: BsAb) has been studied intensively. The bispecific antibody can bind specifically to two different kinds of antigens so that it will be utilized as a therapeutic agent having a specific anti-cancer effect. A diabody (Db) is a minimum unit of the above bispecific antibody. It was developed by utilizing its property that the variable region in a heavy chain (VH) and the variable region in a light chain (VL) derived from the same parent antibody will form a hetero-dimer through non-covalent bond (Non-Patent Document 2).

The diabody-type bispecific antibody is characterized by having low immunogenicity and high infiltrating activity into tumor tissues due to its low molecular weight (ca. 60,000), and by being able to be easily mass-produced at a low cost with use of microorganisms such as E. coli, and to be easily altered in function by means of genetic engineering.

The present inventors already found that the diabody-type bispecific antibody (Ex3) that was produced by utilizing an anti-human epithelial cell growth factor receptor 1 (Her1) antibody 528 and an anti-CD3 antibody OKT3, and its humanized diabody-type bispecific antibody (referred to as "hEx3" in Patent Document 1) showed extremely strong anti-tumor effects. It was further speculated that the structural stability of the variable regions of the above antibodies 528 and OKT3 themselves and their combination are very important for showing such advantageous effects by comparison with an diabody-type bispecific antibody prepared using other antibodies.

Furthermore, the present inventors have developed a highly functional bispecific antibody utilizing said humanized diabody-type bispecific antibody (Patent Document 2).

Methods for the production of bispecific antibodies other than the diabody-type bispecific antibody are described in Non-Patent Documents 3 and 4.

The anti-human epithelial cell growth factor receptor 1 (Her 1) antibody 528 has an effect to inhibit the growth of tumor cells. However, as already described, it is known that when the valency to EGFR is monovalence, the affinity with the antigen will be low and will show only little effect. Actually, no inhibiting effect against tumor cells could be recognized with respect to a single chain antibody (scFV) of the humanized antibody 528. Polymerization of scFV by means of the modification of a linker has been already tried in order to improve said problem of such scFV (Non-Patent Document 5). Recently, a dimer of scFV was reported to induce apoptosis in lymphoma (Non-Patent Document 6). However, there is no report until now about scFV polymers that will show the growth-inhibiting effect against solid cancers or EGFR-positive cancers.

The present inventors have also developed a polymerized low-molecular antibody that consists of scFv based on said anti-human epithelial cell growth factor receptor 1 (Her1) antibody 528, which showed an excellent growth-inhibiting effect against solid cancers (Patent Document 3).

In the prior arts, there have been alternative ways, for example, an addition of polymers such as polyethylene glycol in order to solve the problems such the decrease of half-life in a body and of affinity of the low-molecular antibody, and chemical modification with anti-cancer agent in order to improve the effect of an agent. A lysine residue has been conventionally mutated for the chemical modification of proteins with physiological properties such as an antibody. For example, lysine substitution was successfully done in TNFα by means of phage-display method (Non-Patent Document 7). However, the procedures of this method are not necessarily simple. On the other hand, a lysine residue in a fragment of an antibody can be replaced in a relatively simple way by utilizing a reproductive sequence data base (Non-Patent Document 8).

PRIOR ARTS

Patent Documents

Patent Document 1: Japanese Patent No. 3803790
Patent Document 2: WO 2007/108152 A1

Patent Document 3: Japanese Patent Publication 2010-119303

Non-Patent Documents

Non-Patent Document 1: Rosenburg and Moore (Ed.), "The Pharmacology of Monoclonal Antibodies", Vol. 113, Springer-Verlag, New York, pp. 269-315 (1994)
Non-Patent Document 2: Hollinger, et al., Proc. Natl. Acad. Sci. USA 90, 6444-6448, 1993
Non-Patent Document 3: Alt M, et. al. Novel tetravalent and bispecific IgG-like antibody molecules combining single-chain diabodies with the immunoglobulin gamma1 Fc or CH3 region. FEBS Lett., 454, 90-4. (1999)
Non-Patent Document 4: Lu D, et. al. A fully human recombinant IgG-like bispecific antibody to both the epidermal growth factor receptor and the insulin-like growth factor receptor for enhanced antitumor activity. J Biol Chem., 280, 19665-72. (2005)
Non-Patent Document 5: Biomol. Eng. 2001 18(3): 95-108
Non-Patent Document 6: Biochem Biophysic Res Commun. 2004 315 (4): 912-8
Non-Patent Document 7: Nat Biotechnol. 2003; 21(5):546-52
Non-Patent Document 8: Bioconjug Chem. 2003; 14(2)480-7

Problem to be Solved by the Invention

The lysine reside is most widely used as a target residue for the chemical modification of the proteins. However, since more than one lysines are usually present on the surface of the proteins, it would be difficult to uniformly modify them, which could drastically reduce their activity. Furthermore, in case a lysine in the CDR of an antibody that directly interacts with a target antigen is replaced, it may cause the decrease or loss of its activity. Actually, there has been no success in a site-specifically chemical modification using PEG and the like after replacement of all of the lysine residues except for one lysine residue at a particular site.

Accordingly, a main purpose of the present invention is to provide a variable region fragment of an antibody so as to enable a site-specific modification of one particular lysine residue or N-terminal amino acid.

Means for Solving the Problems

The present inventors have studied hard to solve the above problems, and found that even after all of the lysine residues in the humanized variable region (including CDR) fragment of the anti-human epithelial cell growth factor (EGF) receptor 1 (Her1) antibody 528 had been replaced with other amino acids based on said known reproductive sequence data, its binding activity was sufficiently kept while its affinity was slightly decreased. Furthermore, it was confirmed that the function of the humanized 528 antibody was kept after one of the thus replaced lysine residues in the light or heavy chain had been re-replaced by lysine again taking into a space structure of the above antibody determined by a molecular replacement method. The chemical modification with PEG could then site-specifically add one PEG molecule to a particular site that had been re-replaced into lysine, leading to the completion of the present invention.

The present invention is therefore related to the following aspects:

[1] A lysine-substituted humanized variable region fragment of a light-chain of an anti-human epithelial cell growth factor (EGF) receptor 1 (Her1) antibody 528 (5L) that consists of an amino acid sequence represented by SEQ ID N0:2, wherein all of the lysine residues, or all of the lysine residues except for one lysine residue at a particular site in the humanized variable region of the light chain is replaced by other amino acids.
[2] The lysine-substituted variable region fragment of a light-chain according to Aspect 1, wherein all of the lysine residues except for lysine (Lys) 108 in the 5 L is replaced by other amino acids.
[3] The lysine-substituted variable region fragment of a light-chain according to Aspect 1 or 2, which contains at least one of the following replacements in the 5 L:
Lys 44 is replaced by Arg;
Lys 55 is replaced by Gln;
Lys 79 is replaced by Thr;
Lys 108 is replaced by Glu; or
Lys 112 is replaced by Glu.
[4] The lysine-substituted variable region fragment of a light-chain according to Aspect 1, which contains the following replacements in the 5L:
Lys 44 is replaced by Arg;
Lys 55 is replaced by Gln;
Lys 79 is replaced by Thr;
Lys 108 is replaced by Glu; and
Lys 112 is replaced by Glu.
[5] A lysine-substituted humanized variable region fragment of a heavy-chain of an anti-human epithelial cell growth factor (EGF) receptor 1 (Her1) antibody 528 (5 H) that consists of an amino acid sequence represented by SEQ ID N0:4, wherein all of the lysine residues, or all of the lysine residues except for one lysine residue at a particular site in the humanized variable region of the light chain (5L) is replaced by other amino acids.
[6] The lysine-substituted variable region fragment of a heavy-chain according to Aspect 5, wherein all of the lysine residues except for lysine (Lys) 19 in the 5 H is replaced by other amino acids.
[7] The lysine-substituted variable region fragment of a light-chain according to Aspect 5 or 6, which contains at least one of the following replacements in the 5 H:
Lys 12 is replaced by Ala;
Lys 13 is replaced by Glu;
Lys 19 is replaced by Gln;
Lys 23 is replaced by Ala;
Lys 63 is replaced by Glu; or
Lys 65 is replaced by Gln.
[8] The lysine-substituted variable region fragment of a light-chain according to Aspect 5, which contains the following replacements in the 5H:
Lys 12 is replaced by Ala;
Lys 13 is replaced by Glu;
Lys 19 is replaced by Gln;
Lys 23 is replaced by Ala;
Lys 63 is replaced by Glu; and
Lys 65 is replaced by Gln.
[9] The lysine-substituted variable region fragment of a light-chain or a heavy-chain according to any one of Aspects 1-8, wherein the one lysine residue or N-terminal amino acid is site-specifically modified.
[10] The lysine-substituted variable region fragment of a light-chain or a heavy-chain according to Aspect 9, wherein the one lysine residue or N-terminal amino acid is site-specifically modified with polyethylene glycol.
[11] An antibody molecule comprising as a constituent the lysine-substituted variable region fragment of a light-chain according to any one of Aspects 1-4, 9 or 10, or the lysine-substituted variable region fragment of a heavy-chain according to any one of Aspects 5-8, 9 or 10.

[12] The antibody molecule according to Aspect 11, which is selected from the group consisting of IgG-type antibody molecule, single-chain antibody (scFv), dimer of scFv, bispecific antibody, diabody-type bispecific antibody, highly functional bispecific antibody, and polymerized low-molecular antibody.

[13] The dimmer according to Aspect 12, wherein the one lysine residue contained in the lysine-substituted variable region fragment of a light-chain or a heavy chain is cross-linked.

[14] The diabody-type bispecific antibody according to Aspect 12, wherein the humanized variable region (OL) of a light chain of an anti-CD3 antibody OKT3 and humanized variable region (OH) of a heavy chain of the anti-CD3 antibody OKT3 consist of an amino acid sequence represented by SEQ ID NO: 6 and SEQ ID NO: 8, respectively.

[15] A single-chain polypeptide constituting the antibody molecule of any one of Aspects 11-14.

[16] A nucleic acid molecule encoding the lysine-substituted variable region fragment of any one of Aspects 1-8, or the single-chain polypeptide of Aspect 15.

[17] A nucleic acid molecule encoding both of the two kinds of the single-chain polypeptides constituting the antibody molecule of any one of Aspects 11-14.

[18] A replicable cloning vector or an expression vector containing the nucleic acid molecule of Aspects 16 or 17.

[19] The vector of Aspect 18, which is a co-expression vector.

[20] The vector of Aspect 18 or 19, which is a plasmid vector.

[21] A host cell transformed with the vector of Aspect 19 or 20.

[22] A method for the production of the antibody molecule of Aspect 11 or 12, comprising culturing the host cell according to Aspect 21 to express the two kinds of the single-chain polypeptides constituting said antibody molecule, collecting and purifying said single-chain polypeptides, assembling the two kinds of the single-chain polypeptides, and separating and collecting the antibody molecule thus formed.

[23] The method of Aspect 22 wherein the host cell is *E. coli*, and the two kinds of the single-chain polypeptides are collected from supernatant of a culture medium, periplasm fraction, intracellular soluble fraction or intracellular insoluble fraction.

[24] A method for the production of the antibody molecule of Aspect 14, comprising culturing a host cell transformed with the co-expression vector of Aspect 19 to express the two kinds of the single-chain polypeptides constituting said antibody molecule, allowing the transformed cell to form the diabody-type bispecific antibody in said cell, and separating and collecting the bispecific antibody thus formed.

[25] A pharmaceutical composition comprising the antibody molecule of any one of Aspects 11-14 as an active ingredient.

[26] The pharmaceutical composition of Aspect 25 for use in eliminating, hurting, damaging and/or reducing tumor cells.

Advantages of the Invention

It was confirmed that the lysine-substituted humanized variable region fragment of the light- or heavy-chain of the anti-EGFR antibody and the single-chain antibody constituted based on the fragment had sufficiently maintained binding activity (affinity) for the target cell even a lysine residue contained therein was limited to one at a particular site. As a result, a variety of chemical modifications could be carried out site-specifically and uniformly.

The dimer was prepared by linking the single-chain antibody consisting of the lysine-substituted humanized variable region fragments of the light-chain and the heavy-chain of the anti-EGFR antibody with a chemical cross-linking agent via the lysine residue remained in the single-chain antibodies to show such a growth-inhibiting effect as expected, and an increase in the effect depending on the length of the cross-linking agent as well.

Furthermore, it was confirmed that the humanized diabody-type bispecific antibody comprising the variable region fragment wherein a particular lysine residue had been site-specifically modified with PEG had the same antigen-binding activity as its original humanized diabody-type bispecific antibody.

BRIEF DESCRIPTION OF THE DRAWINGS

The patent or application file contains at least one color drawing. Copies of this patent or patent application publication with color drawing will be provided by the USPTO upon request and payment of the necessary fee.

BEST MODE FOR CARRYING OUT THE INVENTION

Figure 1:
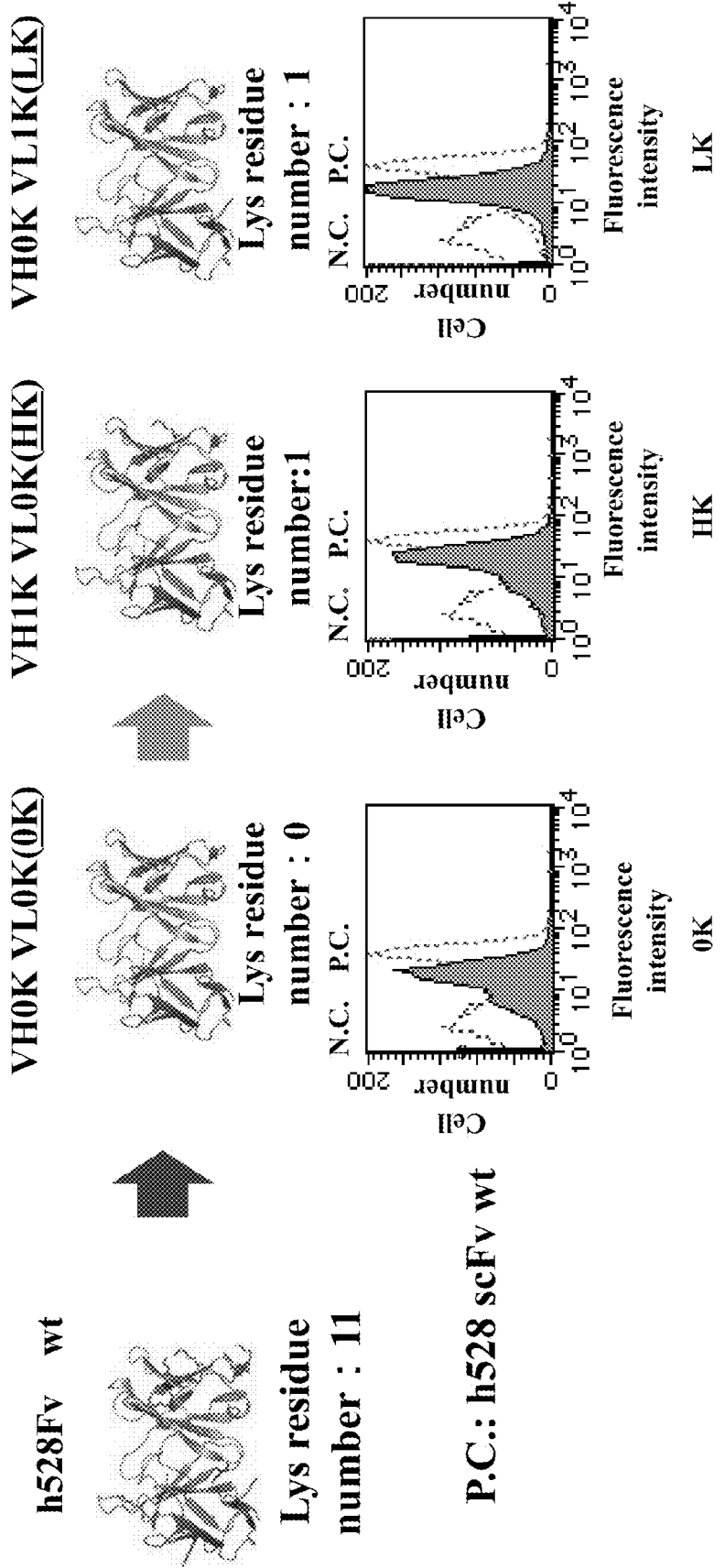
FIG. 1 shows the results of the binding activity of the scFv (lysine-substituted scFv) for A431 cell by means of a flow cytometry.

The lysine-substituted humanized variable region fragment of the light-chain of the anti-EGFR antibody and the lysine-substituted humanized variable region fragment of the heavy-chain of the anti-EGFR antibody (also referred to as a "lysine-substituted variable region fragment") according to the present invention are characterized by that all of the lysine residues, or all of the lysine residues except for one lysine residue at a particular site in the humanized variable region of the light-chain (5L) or the heavy-chain (5H) of the anti-human epithelial cell growth factor (EGF) receptor 1 (Her1) antibody 528 are replaced by other amino acids. The humanized variable region fragments of the light-chain and the heavy-chain consist of an amino acid sequence represented by SEQ ID NO:2 and SEQ ID NO:4, respectively.

5 L contains five lysine residues at positions 44, 55, 79, 108 and 112 in the amino acid sequence represented by SEQ ID NO:2, any one of which positioned at a particular site can be kept as it is. For example, all of the lysine residues except for the lysine reside at the position 108 (Lys 108) was replaced by other amino acids in Example.

5 H contains six lysine residues at positions 12, 13, 19, 23, 63 and 65 in the amino acid sequence represented by SEQ ID NO:4, any one of which positioned at a particular site can be kept as it is. For example, all of the lysine residues except for the lysine reside at the position 19 (Lys 19) was replaced by other amino acids in Example.

There is no limitation on a kind of the amino acids to be substituted for the lysine residue. For example, by referring to a crystalline structure of the humanized antibody 528 or by utilizing the reproductive sequence data base known for those skilled in the art (Non-Patent Document 8), it is possible to select an amino acid with a high probability for the presence at a particular site and to carry out the replacement with the thus selected amino acid by means of a site-specific mutation to give the heavy-chain variable region fragment and the light-chain variable region fragment according to the present invention. It is also possible to prepare the single-chain antibody consisting of said fragments by any method known to those skilled in the art, followed by determination of its binding activity (affinity) for a suitable cell expressing EGFR such as A431 cell (ATCC No. CRL-1555) so as to easily select the one that substantially maintains the activity of said single-chain antibody (h528scFv) before the lysine-substitution.

For example, specific examples for the replacement of each lysine residue in 5L are as follows:
Lys 44 is replaced by Arg;
Lys 55 is replaced by Gln;
Lys 79 is replaced by Thr;
Lys 108 is replaced by Glu; or
Lys 112 is replaced by Glu.

For example, specific examples for the replacement of each lysine residue in 5H are as follows:
Lys 12 is replaced by Ala;
Lys 13 is replaced by Glu;
Lys 19 is replaced by Gln;
Lys 23 is replaced by Ala;
Lys 63 is replaced by Glu; or
Lys 65 is replaced by Gln.

Since all of the above lysine residues, or all of the lysine residues except for one lysine residue at a particular site that may be optionally selected are replaced with the other amino acids in the lysine-substituted variable region fragment according to the present invention, said one lysine residue at the particular site or the N-terminal amino acid may be site-specifically modified under suitable conditions. Thus, the particular lysine residue in the lysine-substituted variable region fragment can be bonded with polyethylene glycol that has a function of preventing the decrease in the half-time of the antibody in a body, decrease in the affinity, and the like (modification with PEG) or with suitable agents such as the anti-cancer agent and radio-active isotopes by utilizing the above site-specific modification.

Various types of antibody molecules may be prepared using as a constituent the lysine-substituted variable region fragment according to the present invention. As an example, there may be mentioned a usual IgG-type antibody molecule, single-chain antibody (scFv), dimer of scFv, bispecific antibody, diabody-type bispecific antibody (Patent Document 1), highly functional bispecific antibody (Patent Document 2), and polymerized low-molecular antibody (Patent Document 3).

The single-chain antibody comprising the lysine-substituted variable region fragment of the light-chain and the lysine-substituted variable region fragment of the heavy-chain according to the present invention may be easily prepared by a prior method. As shown in the Examples below, it has been confirmed unexpectedly from the prior arts that said single-chain antibody comprising only one lysine at the specific site substantially maintains the activity of the original single-chain antibody (h528scFv) before the lysine substitution.

Polymers such as a dimer may be prepared by linking the single-chain antibodies via the lysine residues or the N-terminal amino acid contained in the antibodies. For example, the lysine residue may be present in its light chain or heavy chain. In the case where the lysine residue is present in the heavy chain (HK) or light-chain (LK) of both of the single-chain antibodies constituting the dimmer, a homo dimer represented by "HK-HK" or "LK-LK" will be formed, respectively. On the other hand, if the lysine residue is present in the heavy chain of one of the single-chain antibodies constituting the dimmer, and in the light chain of the other of the above single-chain antibodies, a dimmer "HK-LK" will be produced.

Furthermore, the bispecific antibody may be easily prepared by cross-linking the single-chain antibody according to the present invention with another single-chain antibody having a different antigen specificity.

The cross-linking reaction may be carried out by means of suitable cross-lining agent known for those skilled in the art such as SANH (succinimidyl 4-hydrazinonicotinate acetone hydrazone) and SFB (succinimidyl 4-formylbenzoate). The distance between the single-chain antibodies may be freely controlled with cross-linking agenst having a different cross-linking distance. Furthermore, a polyvalent molecule may be also prepared by using a cross-linking agent having a high branching number.

Specific structures and it preparation method that are comprised in the humanized highly functional bispecific antibody (BsAb) are disclosed in detail in WO 2007/108152 A1 (Patent Document 2). There is no limitation on the constant region or Fc region comprised in the present antibodies as long as it is derived from the human antibody. For example, CL may be derived from κ or λ chain. Fc region or the heavy chain constant region is usually derived from γ chain of IgG. The amino acid sequences represented by SEQ ID NOS: 29, 30 and 33 disclosed in Patent Document 2 are representative examples of CH1, CH2 & CH3, and CL, respectively.

Figure 3:
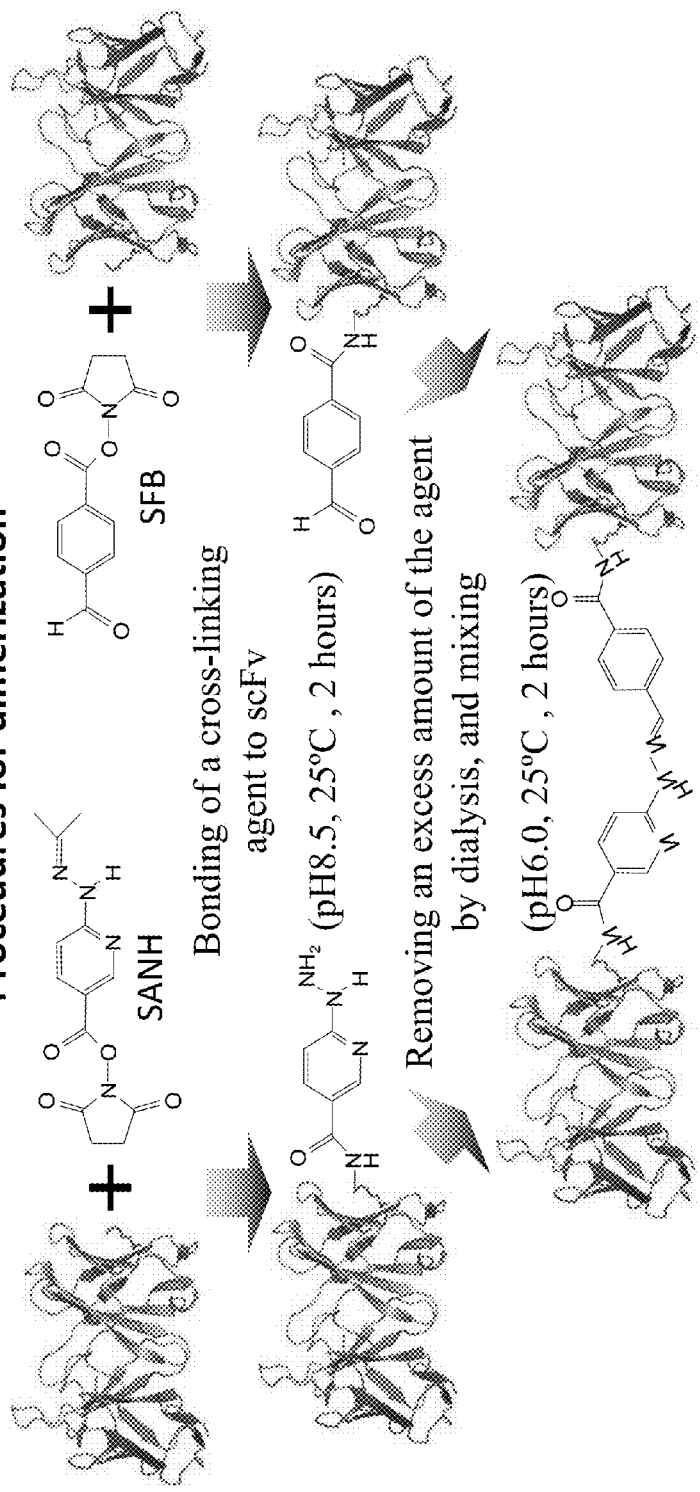
FIG. 3 shows a method for the dimerization of the lysine-substituted scFv.
Figure 3:
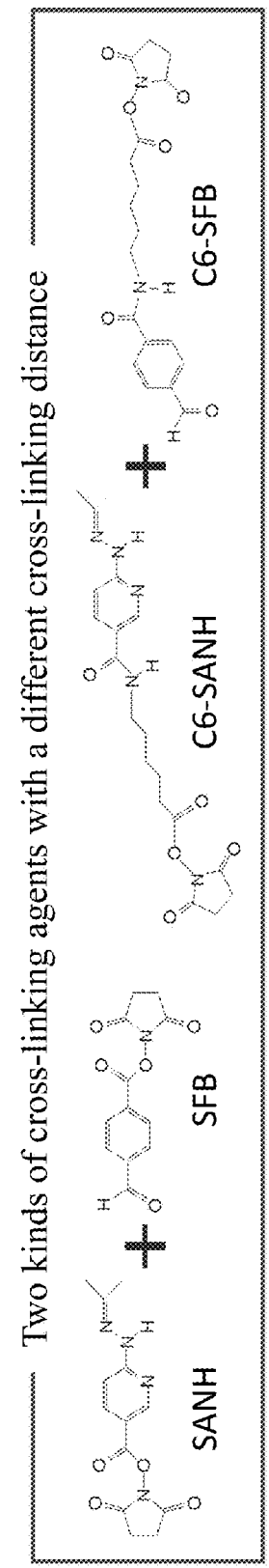
Figure 4:
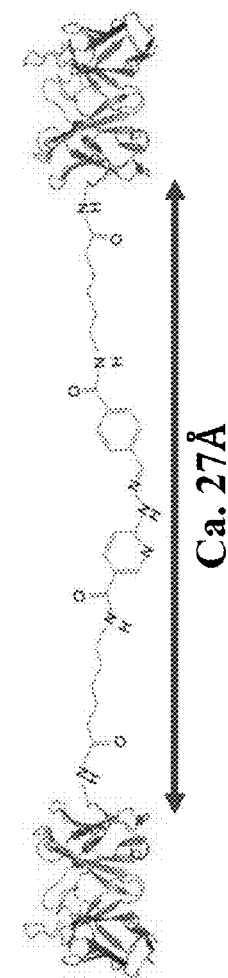
FIG. 4 shows the cell growth-inhibiting activity of the dimer of the lysine-substituted scFv.
Figure 4:
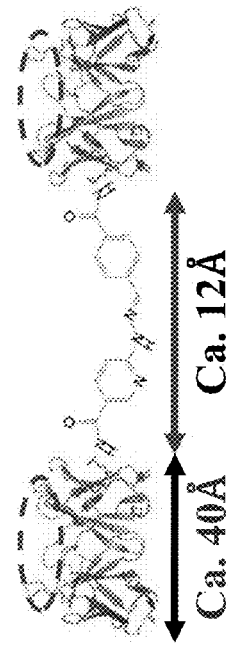
Figure 4:
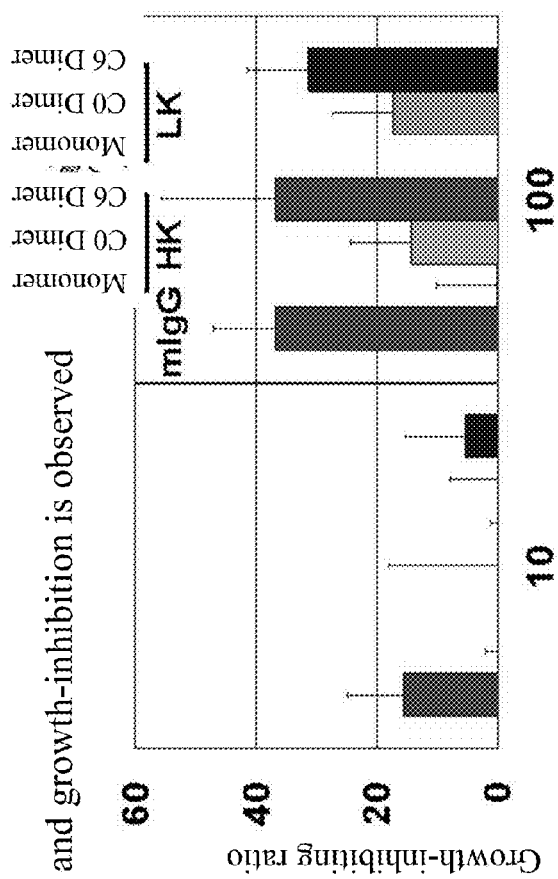

Representative examples of the amino acid sequences of the PreSission sequence, hinge region, peptide linker, signal peptide, etc. that are comprised in the single-chain polypeptides constituting the BsAb are shown in FIGS. 3-3 and 3-4 of Patent Document 2. The PreSission sequence comprises a protease-cleavage site. There is no limitation on the kind of protease used in the present invention, and any enzyme known in the art such as Thrombin and Factor Xa may be used, and the amino acid sequence comprising the protease-cleavage site may be optionally selected.

Furthermore, the present invention include the humanized diabody-type bispecific antibody, humanized highly functional bispecific antibody wherein a light chain variable region is located at the N-terminal side of a heavy variable region (LH type) in each polypeptide constituting said antibodies. Like in the lysine-substituted variable region fragment according to the present invention, it is possible to prepare a total lysine-substituted heavy chain and light-chain variable region fragments of the anti CD3 antibody, wherein all of the lysines contained in the fragments have been replaced with other amino acids based on the reproductive sequence database, and to combine it with the lysine-substituted variable region fragment according to the present invention, so that various kinds of the bispecific antibodies may be constructed.

Patent Document 3 discloses the polymerized low-molecular antibody consisting of the above single-chain antibodies (scFv). For example, the polymerized low-molecular antibody may be formed by assembling 2-4 single-chain antibodies, wherein one or several amino acids at C-terminus of the lysine-substituted variable region fragment that is located on N-terminal side in each scFv may be removed, and one or several amino acids at N-terminus of the lysine-substituted variable region fragment that is located on C-terminal side in each scFv may be removed as well. Accordingly, the single-chain antibody comprising the lysine-substituted variable region fragment of the light-chain or heavy-chain according to the present invention can be also used as a constituent of the polymerized low-molecular antibody disclosed in Patent Document 3.

Furthermore, each of the antibodies mentioned above, which comprises as its constituent the lysine-substituted variable region fragment that has been site-specifically modified with PEG, for example, of the present invention, may be easily prepared by constructing an antibody comprising the lysine-substituted variable region fragment according to the present invention, followed by a suitable chemical modification such as that with PEG.

Mouse B cell hybridoma 528 producing the anti-EGFR antibody (ID:TKG0555) is deposited in Cell Resource Center for Biomedical Research, Institute of Development, Aging and Cancer of TOHOKU University. The above hybridoma 528 producing anti-EGFR antibody is also stored at ATCC with an ATCC Accession No. HB-8509, so that it may be obtained from these deposit authorities.

On the other hand, the anti-CD3 antibody, OKT3 (ID: TKG0235) is deposited in Cell Resource Center for Biomedical Research, Institute of Development, Aging and Cancer, of TOHOKU University, and is also stored at ATCC with an ATCC Accession No. CRL-8001, so that it may be obtained from these deposit authorities.

cDNA may be prepared by known methods. For example, mRNA is extracted with ISOGEN (Nippon Gene Co.) and then cDNA is prepared by means of First-Strand cDNA Synthesis Kit (Amersham Biosciences Co.). PCR reaction is done for the cDNA using cloning primers that are synthesized in accordance with the disclosure of a Reference document (Krebber, A. et al. Reliable cloning of functional antibody variable domains from hybridomas and spleen cell repertoires employing a reengineered phage display system. J Immunol Methods 201, 35-55. (1997)) so as to determine the sequences of the variable regions of H and L chains of each antibody.

The term "humanized" variable region as used in the lysine-substitued variable region fragment or the single-chain antibody constituting the antibodies according to the present invention means a human immunoglobulin (a recipient antibody) in which at least a part of the residues of complementary determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in either the recipient antibody or the introduced CDR or framework. These changes are made in order to optimize or improve the properties of the resulting antibody. More detailed information on these changes are referred to Jones et al., Nature 321, 522-525 (1986); Reichmann et al., Nature 332, 323-329 (1988); EP-B-239400; Presta, Curr. Op. Struct. Biol 2, 593-596 (1992); and EP-B-451216.

The humanization of the variable region of the antibody may be prepared in accordance with any methods known to those skilled in the art, for example, by analyzing various conceptual humanized preparations based on three-dimensional immunoglobulin models of the recipient antibody and donor antibody, and analyzing them. The three-dimensional immunoglobulin models are well known in the art, being referred to, for example, WO92/22653.

Thus, one example of the humanized variable region according to the present invention is an antibody wherein the complementary determining regions (CDR) in the variable regions are derived from a mouse antibody, and the other parts are derived from a human antibody.

The activity or function of the resulting antibody may be deteriorated due to the humanization. The activity or function of the humanized antibody according to the present invention may be therefore improved by being provided with a site-specific mutation at an appropriate position in the single-chain polypeptide, for example, at a position in the framework which can affect the CDR structure, such as in canonical sequence or vernier sequence.

Specifically, the humanization of the variable regions of 528 was performed by means of CDR grafting. Thus, a human antibody having FR (Frame Work) with the highest homology was screened and selected by a homology search in view of the length of each CDR and the like. An amino acid sequence was designed, in which the CDR of the selected human antibody was replaced with CDR of 528. The total gene may be then synthesized by means of overlapping PCR by preferably using the optimum codons for E. coli.

It was already reported that the variable region of the humanized OKT3 could maintain its activity when compared with the mouse OKT3 (Adair, J. R. et al. Humanization of the murine anti-human CD3 monoclonal antibody OKT3. Hum Antibodies Hybridomas 5, 41-7. (1994)). The total gene was synthesized by means of overlapping PCR based on the amino acid sequence of the variable regions of the humanized OKT3 disclosed in the above document. The optimum codons for E. coli were used in the synthesis. It was also reported that the use of the gene containing the optimum codons would increase the expression level in E. coli.

The humanized variable region of the light chain (5L) and the humanized variable region of the heavy chain (5H) of the anti-human EGF receptor 1 antibody 528, and the humanized variable region of the light chain (OL) and the humanized variable region of the heavy chain (OH) of the anti-CD3 antibody OKT, which are a basic element for the various kinds of the antibody molecule of the present invention may have a nucleotide sequence and an amino acid sequence represented by SEQ ID NOS:1 and 2, 3 and 4, 5 and 6, and 7 and 8, respectively.

It is preferred that the lysine-substituted variable region fragments of the heavy-chain and light-chain in the single-chain polypeptide are linked via an appropriate peptide linker. Any linker known in the art or one modified therefrom may be optionally selected and used in the present invention as long as it makes hard for the fragments to interact within its molecule so that it will enable the formation of a polymer of plurality of the single-chain antibodies. As a result, the VH and VL derived from different single-chain antibodies with each other shall assemble appropriately so as to form a structure that mimics or improves the function of an original protein (the function originated or derived from the original polypeptide or protein) such as all or part of its biological activity. The peptide linker according to the present invention may have about 1-20 amino acids, preferably about 1-15 amino acids, more preferably about 2-10 amino acids.

Alternatively, the two humanized variable regions may be directly linked with each other in the single-chain polypeptide. In such case, one or a few amino acids located at C-terminus of the humanized variable region fragment of the N-terminal side, or one or a few amino acids located at N-terminus of the humanized variable region fragment of C-terminal side are preferably deleted in order to increase three-dimensional degree of freedom in each single-chain antibody and to improve their polymerization.

The polypeptide having an amino acid sequence in which one or a few (for example, 1-5, or 1-3) amino acids are substituted, deleted, inserted or added in the amino acid sequences represented by the above SEQ ID NOS, and having substantially the same property and function as that of the polypeptide having the original amino acid sequence such as an antigen specificity as that of the lysine-substituted variable region fragment according to the present invention may be also used as the single-chain polypeptide constituting the present antibody molecule. However, the amino acid mutation in SEQ ID NO:4 of the present lysine-substituted variable region fragment shall be maintained. It is preferable to make a substitution among amino acids belonging to the same group (polar, non-polar, hydrophobic, hydrophilic, positive-charged, negative-charged, or aromatic amino acid group), or to make a deletion or addition of amino acid so as not to cause a substantial difference or effects with respect to the three-dimensional or local charge-condition of the protein. Such polypeptides having the substitution, deletion or addition of the amino acid(s) my be easily prepared by well known methods such as site-specific mutation (point mutation method or cassette mutation), genetic homologous recombination, primer extension method and PCR, or any optional combinations thereof. The above amino acid sequence comprising one or few amino acids that are substituted, deleted, inserted or added have homology (identity) of 90% or more, preferably 95% or more, more preferably 99% or more with a full-length amino acid sequence in the original amino acid sequence.

The representative examples of the nucleic acid molecules (oligonucleotides) encoding each part or amino acid sequence of the lysine-substituted variable region fragment and the single-chain antibody comprised in the antibody molecules according to the present invention have the nucleotide sequences shown in the above SEQ ID NOs. Furthermore, as a nucleic acid molecule with the nucleotide sequence having homology of 90% or more, preferably 95% or more, more preferably 99% or more with a full-length nucleotide sequence represented by the same SEQ ID NOS are considered to encode a polypeptide having substantially the same property and function as that of the original polypeptide or part thereof, the above nucleic acid molecule is included in the nucleic acid molecule of the present invention. However, the amino acid mutation in SEQ ID NO:4 of the present lysine-substituted variable region fragment shall be maintained. Although the nucleic acid molecule comprises a nucleotide sequence encoding at least either of the two kinds of the single-chain polypeptides constituting the antibodies such as diabody-type bispecific antibody according to the present invention, it preferably comprises two kinds of nucleotide sequences together, each of which encodes one of the two kinds of said single-chain polypeptides, respectively.

In order to determine the homology between two amino acid or nucleotide sequences, they may be preliminarily treated into an optimum condition for comparison. For example, a gap may be inserted into one of the sequences to optimize the alignment with the other sequence, followed by the comparison of amino acid or nucleotide at each site. When the same amino acid or nucleotide exists at a corresponding site of the first and second sequences, these two sequences are considered to be identical with respect to said site. Homology between two sequences is shown by a percent ratio of the number of the identical sites over the total number of amino acids or nucleotides between the two sequences.

The term "homology (or "identity") in this specification means an amount (or a number) of the amino acids in an amino acid sequence or the nucleotides in a nucleotide sequence, which are determined to be identical with each other in the relationship between two sequences, showing an extent of the correlation between the two polypeptide or nucleotide sequences. The homology may be easily calculated. The term "homology" or "identity" is well known in the art, and many methods for the calculation of such homology are known, among them. For example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991). A general method for the determination of the homology between two sequences is disclosed, for example, in Martin, J. Bishop (Ed.), Guide to Huge Computers, Academic Press, San Diego, (1994); Carillo, H. & Lipman, D., SIAM J. Applied Math., 48: 1073 (1988). A preferable method for the determination of the homology between two sequences is, for example, one designed to obtain a largely related part between said two sequences. Some of them are provided as a computer program. Preferable examples of the computer programs for the determination of the homology between two sequences include GCG program package (Devereux, J. et al., Nucleic Acids Research, 12(1): 387 (1984)), BLASTP, BLASTN, FASTA (Atschul, S. F. et al., J. Molec. Biol., 215: 403 (1990).

The nucleic acid of the present invention further includes a DNA molecule that hybridizes with a DNA comprising a nucleotide sequence complementary to the nucleotide sequence represented by the above SEQ ID NOs under stringent conditions, and encodes a polypeptide having substantially the same property and function as that of the polypeptides represented by the above SEQ ID NOs.

Hybridization may be carried out by or in accordance with a method well known in the art such as that described in Molecular cloning third. ed. (cold Spring Harbor Lab. Press, 2001). Hybridization may be done in accordance with an instruction or manual attached to a commercially available library.

Hybridization may be carried out by or in accordance with a method well known in the art such as that described in Current protocols in molecular biology edited by Frederick M. Ausbel et al., 1987). Hybridization may be done in accordance with an instruction or manual attached to a commercially available library.

The phrase "stringent conditions" in this specification may be defined by a suitable combination of salt concentration, organic solvent (for example, formamide), temperature, and other known conditions. Thus, stringency will be increased by the decrease of salt concentration, or the increase of an organic solvent concentration or hybridization temperature. The washing conditions after the hybridization may also affect the stringency. The washing conditions are also defined by salt concentration and temperature. The stringency of washing will be increased by the decrease of salt concentration or the increase of temperature.

Accordingly, the "stringent conditions" in this specification means conditions under which a specific hybrid can be formed only between the nucleotide sequences having homology of about 80% or more, preferably about 90% or more, more preferably about 95% or more on a total average. Specifically, they may be sodium concentration of 150-900 mM, preferably 600-900 mM, pH6-8 at 60-68° C. One example of the stringent conditions is hybridization in 5×SSC (750 mM NaCl, 75 mM $Na_3$ Citirate), 1% SDS, 5× Denhart solution 50% formaldehyde at 42° C., followed by the washing with 0.1×SSC (15 mM NaCl, 1.5 mM $Na_3$ Citirate), 0.1% SDS at 55° C.

Furthermore, the nucleic acid encoding the lysine-substituted variable region fragment in the single-chain antibody may be synthesized by means of an over-lapping PCR method based on a pre-determined amino acid sequence. The nucleic acid used herein has no limitation in its chemical structure or preparation route, as long as it is a molecule encoding the single-chain polypeptide, including gDNA, cDNA chemically-synthesized DNA and mRNA.

Specifically, the nucleic acid according to the present invention may be isolated from cDNA library by means of hybridization or PCR based on the sequences disclosed in literatures. The thus isolated DNA may be inserted in an expression vector, with which a host cell such E. coli, COS cell, CHO cell or myeloma not expressing immunoglobulin are transfected to synthesize a monoclonal antibody in the thus transformed host cells. PCR may be carried out in accordance with a method known in the art, or substantially the same or altered methods. The methods disclosed in, for example, R. Saiki, et al., Science, 230:1350, 1985; R. Saiki, et al., Science, 239:487, 1988; H. A. Erlich ed., PCR Technology, Stockton Press, 1989; D. M. Glover et al., ed., "DNA Cloning," $2^{nd}$. ed., Vol. 1, (The Practical Approach Series), IRL Press, Oxford University Press (1995); M. A. Innis et al., ed., "PCR Protocols: a guide to methods and applications," Academic Press, New York (1990); M. J. McPherson, P. Quirke and G. R. Taylor (Ed.), PCR: a practical approach, IRL Press, Oxford (1991); M. A. Frohman e al., Proc. Natl. Acad. Sci. USA, 85, 8998-9002 (1988), and their modified and altered methods may be used in the present invention. PCR may be performed with use of a commercially available kit in accordance with manufacturer's protocols.

The sequencing method of nucleic acids such as DNA may be referred to Sanger et al., Proc. Natl. Acad. Sci. USA 74:5463-5467 (1977). A general method for recombinant DNA techniques may be referred to J. Sambrook, E. F. Fritsch & T. Maniatis (ed.), "Molecular Cloning: A Laboratory Manual ($2^{nd}$ edition)", Cold Spring Harbor Laboratory Press, Cold Spring Harbor, New York (1989) and D. M. Glover et al. (ed.), $2^{nd}$ ed., Vol. 1 to 4 (The Practical Approach Series), IRL Press, Oxford University Press (1995).

The nucleic acid encoding the single-chain polypeptide constituting the present antibody molecule or each region comprised therein may be modified or altered so that it will optionally encode a desired peptide or amino acid depending on the purpose. The techniques for such modification or alternation are disclosed in Mutagenesis: a Practical Approach, M. J. McPherson (ed.), IRL Press, Oxford, UK (1991), including a site-specific mutagenesis introduction method, cassette mutagenesis induction method and PCR mutagenesis method.

The term "modification (or alternation)" as used herein refers to insertion, deletion or substitution of base(s) in at least one codon encoding an amino acid residue in the originally obtained nucleic acid. It includes alternation of the amino acid sequence per se of the single-chain polypeptide by replacing a codon encoding the original amino acid with a codon encoding another amino acid.

Alternatively, the nucleic acid encoding the single-chain polypeptide may be altered without changing the amino acid per se, by using a codon suitable for a host cell such as E. coli (an optimum codon). With the use of the optimum codon, expression efficiency of the single-chain polypeptide in the host cell will be improved.

The antibody molecule according to the present invention may be produced by various methods well known in the art such as genetic engineering technique and chemical synthesis. For example, the genetic engineering technique includes producing a replicable cloning vector or an expression vector containing the nucleic acid molecule encoding each of the two kinds of the single-chain polypeptides constituting the above bispecific antibody, transforming a host cell with the vector, culturing the transformed host cell to express each of the single-chain polypeptides, collecting and purifying said single-chain polypeptides, assembling the two kinds of the single-chain polypeptides, and separating and collecting the bispecific antibody thus formed.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which can not be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium. Furthermore, various peptide tags (c-myc and His-tag, for example) known in the art may be contained at its end, etc.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned prokaryotic cells such as including E. coli., eukaryotic cells such as mammalian cells such Chinese hamster ovary (CHO) cell and human cells, yeast, and insect cells. For example, BL21 star (DE3) strain is cultured in 2×YT culture medium at about 28° C. and induced with IPTG of about 0.5 mM, so that the yield of the present antibody molecule may be highly improved so as to increase its production efficiency.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea. The present antibody molecule is produced by assembling or rewinding the two kinds of the single-chain polypeptides thus purified, and separating and collecting the thus formed antibody molecule.

Assembling treatment will bring a single-chain polypeptide back in its appropriate spatial arrangement in which a desired biological activity is shown. Since this treatment may also bring polypeptides or domains back into their assembling state, it may be considered "re-assembling." It may be also called "re-constitution" or "refolding" in view of gaining the desired biological activity. The assembling treatment may be carried out by any method known in the art, preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the present highly functional BsAb thus formed may be done by any method known in the art as well.

As already described above, the antibody molecule according to the present invention may be prepared from the supernatant of a culture medium, periplasm fraction, intracellular soluble fraction and intracellular insoluble fraction.

It is possible to transform a host cell with the co-expression vector containing a nucleic acid molecule encoding both of the two kinds of the single-chain polypeptides constituting the antibody molecule of the present invention, or with the two kinds of a expression vector containing a nucleic acid molecule encoding each of the two kinds of said single-chain polypeptides, respectively, culturing the transformed host cell so as to express the two kinds of the single-chain polypeptides, allowing the transformed cell to form the antibody molecule in said cell, and separating and collecting it from supernatant of the culture medium or intracellular soluble fraction. In such case, the above assembling or rewinding treatment is unnecessary so that a high productivity can be achieved at a low cost.

Furthermore, it is preferable to culture BL21 star (DE3) strain (Invitrogen) as a host cell in 2×YT culture medium with shaking at 28° C. overnight, to induce with IPTG at a final concentration of 0.5 mM when O.D at 600 nm becomes about 5, and to collect the desired protein 16 hours later of the induction from the supernatant of the culture medium and periplasm fraction after an osmotic pressure treatment.

A pharmaceutical preparation according to the present invention comprises an active ingredient selected from the group consisting of the present antibody molecule, the single-chain polypeptide, the nucleic acid, the vector, and the host cell described in the above. As shown by the examples in the present specification, since the active ingredient has an activity of eliminating, hurting, damaging and/or reducing tumor cells expressing EGFR in vitro and in vivo, the present pharmaceutical preparation is used as an anti-tumor agent.

An effective amount of the active ingredient may be optionally determined by those skilled in the art depending on the purpose of treatment, medical conditions of a patient to be treated such as kind, site or size of tumor, and administration route. A typical dose or daily dose may be first determined in vitro by using an assay method of growth or existence of the tumors known in the art, then determined with use of such an appropriate animal model as to allow extrapolation of the resulting dose range to human patients.

The pharmaceutical preparation of the present invention may optionally comprise various kinds of pharmaceutically acceptable components known in the art such as carrier, excipient, buffer, stabilizing agent and the like, depending on various factors such as the kind of the active ingredients, its formulation form, the route and purpose of administration, medical conditions of patient.

The pharmaceutical preparation of the present invention may be formulated into any form such as pill, liquid, powder, gel, air spray, microcapsule, and colloidal dispersion (liposome, micro emulsion, etc.).

The pharmaceutical preparation may be administered by injecting or infusing intraveneously, intraperitoneally, intracerebrally, intraspinally, intramuscularly, intraocularly, intraarterially, especially intrabiriarily, or via diseased tissue, or with use of a constant releasing agent system. The active ingredient according to the present invention may be administered through continuous fluid infusion or massive injection. The pharmaceutical preparation according to the present invention is preferably administered in combination with the cell having phagocytosis or cytotoxic activity. Alternatively, the active ingredient such as the present BsAb may be mixed with the above cells so as to bind to them before its administration.

The constant releasing agent generally refers to a formulation that can release the active ingredient of the present invention for a certain period of time. One of the preferred constant releasing agents comprises a semi-permeable carrier of solid hydrophobic polymer such as protein, which is shaped into a form such as film or micro capsule.

The pharmaceutical preparation according to the present invention may be produced by a method that is optionally selected from, for example, "Guide Book of Japanese Pharmacopoeia", Ed. of Editorial Committee of Japanese Pharmacopoeia, Version No. 13, published Jul. 10, 1996 by Hirokawa publishing company The terms as used in the present specification and drawings are based on IUPAC-IUB Commission on Biochemical Nomenclature or on meanings of the terms conventionally used in the art.

The present invention will be explained in more detail by referring to the Examples, which are provided only for describing the specific embodiments of the present invention, but not for limiting the scope of the present invention. It is therefore to be understood that various embodiments based on the inventive concept of the present specification may be practiced within the scope of the present invention.

The following examples were or can be carried out with standard techniques well known to those skilled in the art unless otherwise described. Thus, unless otherwise described, specific procedures and treating conditions are in accordance with J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995) (DNA cloning), and with H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990) (PCR). A commercially available agent and kit were used in accordance with protocols attached thereto.

EXAMPLE 1

Production of a Lysine-substituted Humanized Variable Region Fragment of the Anti-human EGF Receptor 1 (Her1) Antibody 528

The crystal structure of the humanized antibody 528 was first determined by means of Molecular Replacement method. The results are shown in Table 1. Referring to the thus obtained structure and the reproductive sequence database (Non-Patent Document 8), all of the lysine residues including those contained in CDR were replaced with other suitable amino acids in the light-chain humanized variable region (5L) represented by SEQ ID No:2 and the heavy-chain humanized variable region (5H) represented by SEQ ID No:4 of the anti-human EGF receptor 1 antibody 528.

TABLE 1

| Crystallographic Data | | |
|---|---|---|
|  | Humanized 528 | Mouse 528 |
| Space group | $P6_5$ | $P6_2$ |
| Unit cell dimension (Å) | a = b = 63.28 | a = b = 126.60 |
|  | c = 225.34 | c = 68.28 |
| Resolution (Å) | 2.1 | 2.3 |
| R factor | 0.27 | 0.19 |
| Free R factor | 0.30 | 0.23 |

As a result, the variable region 5 H (VH0K) and the variable region 5 L (VL0K) wherein all of the lysine residues had been replaced with the following amino acids were obtained as an example of the lysine-substituted variable region fragment.

Replacement of the lysine residue in 5 L:
Lys 44 is replaced by Arg;
Lys 55 is replaced by Gln;
Lys 79 is replaced by Thr;
Lys 108 is replaced by Glu; or
Lys 112 is replaced by Glu.

Replacement of the lysine residue in 5H:
Lys 12 is replaced by Ala;
Lys 13 is replaced by Glu;
Lys 19 is replaced by Gln;
Lys 23 is replaced by Ala;
Lys 63 is replaced by Glu; or
Lys 65 is replaced by Gln.

Then, the glutamate residue (Gln) at the position 19 of 5H and the glutamic acid residue (Glu) at the position 108 of 5L were re-replaced with a lysine residue to give the lysine-substituted humanized variable region fragments of the heavy-chain (VH1K) and the light-chain (VL1K) of the anti-human epithelial cell growth factor (EGF) receptor 1 (Her1) antibody 528, respectively.

EXAMPLE 2

Production of a Single-chain Antibody (scFv) Comprising the Lysine-substituted Variable Region Fragment We then prepared three kinds of lysine-substituted single-chain antibodies (scFv): "OK" containing "VH0K" and "VL0K"; "HK" containing "VH1K" and "VL0K"; and ""LK" containing "VH0K" and "VL1K" as follows.

An expression vector was constructed based on the humanized 528scFv-expression vector (pRA-h5Hh5L(G1), Patent Document 3). Thus, each vector was digested with a restriction enzyme NcoI and EagI, and the site of h5H or h5L, which included a linker sequence, was exchanged with each fragment to give a humanized scFv-expression vector having 15-amino acid linker (GGGGS)3. A His-tag (Hisx6: histidine hexamer tag) had been introduced tandem into its C-terminal for purification, respectively. The resulting vector was expressed in a host *E. coli* to give the single-chain antibody according to the present invention.

The binding activity of the scFv for the human epidermoid cancer cell, A431 (ATCC No. CRL-1555) was detected with flow cytometry. Target cell was mixed with 100 pmol of each scFv, left to stand still for 30 min. at 4° C., washed twice with 0.1% $NaN_3$/PBS, mixed with a second antibody of rabbit antiserum immunized with the Ex3 diabody followed by the same procedures, and finally mixed with a third antibody of FITC-conjugate anti-rabbit antibody followed by the same procedures, and subjected to the detection of fluorescence. 0.1% $NaN_3$/PBS was added instead of the first antibody for a negative control (NC), and h528scFv (SEQ ID NO:9, 10) was used instead of the first antibody for a positive control (referred to as "PC"). The results are shown in FIG. 1.

Furthermore, a rate analysis of the scFv by SPR method (J Biol Chem. 2010 Jul. 2; 285 (27)20844-9) gave the following results.

TABLE 2

|  | kon[1/Ms] | koff[1/s] | KA[1/M] |
|---|---|---|---|
| h528 scFv | $1.41 \times 10^5$ | $5.42 \times 10^{-3}$ | $2.61 \times 10^7$ |
| VH0K VL0K | $6.03 \times 10^4$ | $8.24 \times 10^{-3}$ | $7.32 \times 10^6$ |
| All lysine was replaced |  |  |  |
| VH1K VL0K | $7.10 \times 10^4$ | $8.05 \times 10^{-3}$ | $8.82 \times 10^6$ |
| H19 was re-replaced with lysine |  |  |  |
| VH0K VL1K | $7.11 \times 10^4$ | $8.53 \times 10^{-3}$ | $8.34 \times 10^6$ |
| L108 was re-replaced with lysine |  |  |  |

It was then confirmed from the above results that the binding activity of the three single-chain antibodies according to the present invention for A431 cell was substantially the same (or was maintained) as that of h528scFv before the lysine-substitution.

EXAMPLE 3

Figure 2:
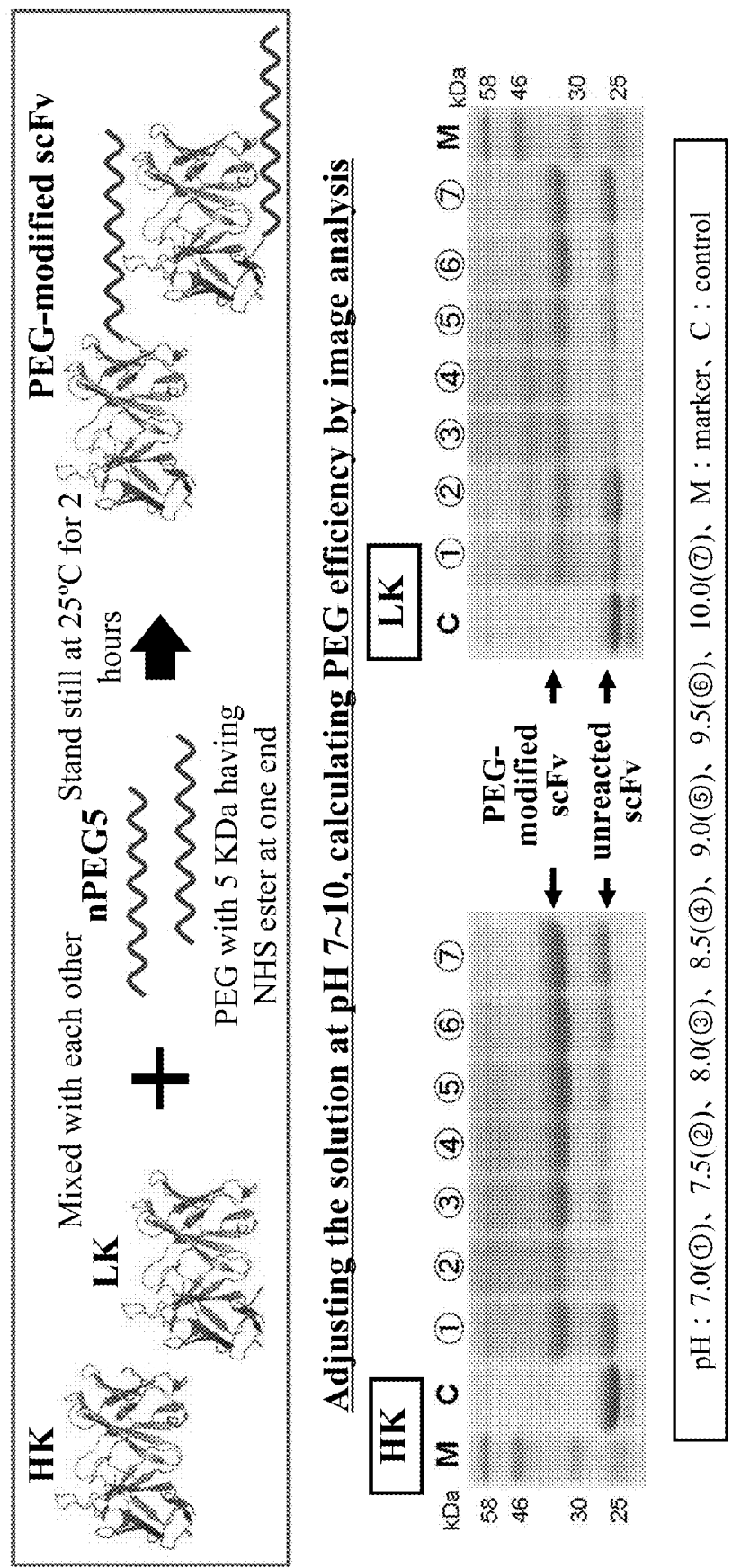
FIG. 2 shows modification of the lysine-substituted scFv with PEG.

PEG Modification of the Single-chain Antibody (scFv) Comprising the Lysine-substituted Variable Region Fragment A particular lysine residue contained in the HK or LK prepared in Example 2 was site-specifically modified with PEG by mixing Gdn-HCl/PBS solution containing 20 μM of said HK or LK and PEG of 5 kDa (2 mM) having NHS ester at its one end and letting the mixture stand still for 2 hours at 5° C. (pH 7-10), and subjected to SDS-PAGE. The results shown in FIG. 2 indicate that the site-specific PEG-modification could be obtained at pH 8.5 with a high efficiency (about 64-73%).

EXAMPLE 4

Production of a Dimer Consisting of the Single-chain Antibodies Comprising the Lysine-substituted Variable Region Fragment The dimerization of the two scFv, HK and LK was carried out using SANH (succinimidyl 4-hydrazinonicotinate acetone hydrazone) and SFB (succinimidyl 4-formylbenzoate) as a cross-linking agent. SANH is a molecule having NHS ester at one end and a hydrazine group at the other end. SFB is a molecule having NHS ester at one end and an aldehyde group at the other end. After having linked these agents with HK and LK, respectively, the resulting HK or LK linked with SANH and the resulting LK or HK linked with SFB were mixed to give a dimer antibody due to the formation of a hydrazone bonding. Thus, the scFv was first dialysed against borate buffer (pH 8.5, 25° C.) and mixed with SANH or SFB (20 mM) in dimethylsulfoxide (DMSO) to a final concentration of 2 mM (10% DMSO) so as to stand still for two hours at 25° C. After having been dialyzed against a buffer with pH 7.0 or less for two hours in order to simultaneously remove an excess amount of SANH or SFB and change the pH value, the scFv linked with SANH or SFB were mixed (pH 6.0 (PBS)) so as to stand still for two hours at 25° C. for the formation of the dimer (FIG. 3). By using cross-linking agents having a different cross-linking distance, dimers having different distance between each scFv could be prepared.

The dimers according to the present invention were subjected to MTS assay with respect to their growth-inhibiting activity against A431 (ATCC No. CRL-1555).

Each cell sample was adjusted by cell counting to contain $2 \times 10^3$ cells per 100 μL of RPMI 1640 (0.5% FBS), and its aliquot of 100 μL was dispensed into each well of a 96-well plate to stand still overnight at 37° C. After being diluted with RPMI to a desired concentration of the antibody according to the present invention, 2004 of which was put into each well of the above plate, and cultured for 96 hours at 37° C. After the culture medium was removed, the cells were washed with PBS, mixed with MTS, PMS and RPMI, and incubated for 30-60 min. at 37° C., followed by the detection of absorbance at 490 nm with a plate reader. The results shown in FIG. 4 indicate that the dimers according to the present invention induced the cell growth-inhibiting activity that could not effected by the monomer (HK or LK).

NOTE: MTS (CellTiter 96 AQueous Non-Radioactive Cell Proliferation Assay, Promega Co.); and
PMS (CellTiter 96 AQueous Non-Radioactive Cell Proliferation Assay, Promega Co.).

EXAMPLE 5

The Production of the PEG-modified Diabody-type Bispecific Antibody

The diabody-type bispecific antibody was then prepared in accordance with the method disclosed in Patent Document 1. First, a single-chain polypeptide (528 VL 1K (Lys108)- OKT3 VH Lys(-)) was prepared, which consisted of the lysine-substituted variable region fragment of the light chain (VL1K) of the present invention and a totally lysine-substituted humanized heavy-chain variable region of the anti-CD3 antibody OKT3 (OH) represented by SEQ ID NO:8 wherein all of the lysine residues were replaced with other amino acids. The resulting single-chain polypeptide was then modified with PEG under the conditions (pH 8.5) in Example 3 to give a PEG-modified single-chain polypeptide wherein only Lys 108 of the light-chain variable region of the 528 antibody was site-specifically modified with PEG.

Similarly, a single-chain polypeptide (528 VH-OKT3 VL) was prepared, which consisted of the humanized heavy chain of the 528 antibody represented by SEQ ID NO: 4 and the humanized light-chain variable region of the anti-CD3 antibody OKT3 (OH) represented by SEQ ID NO:6.

Figure 5:
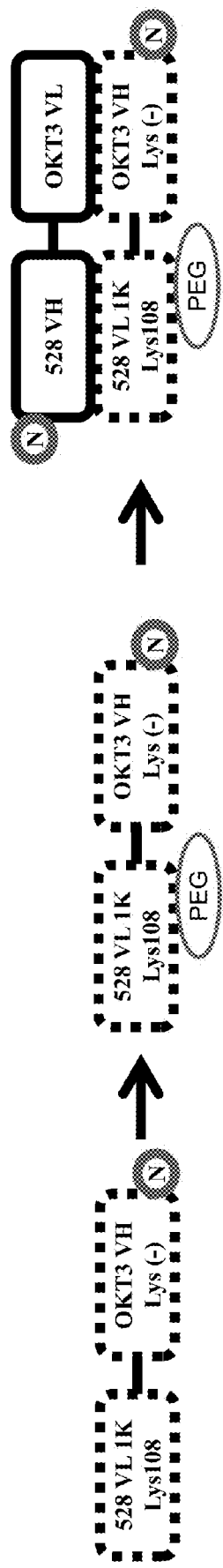
FIG. 5 shows a process of preparation of the PEG-modified humanized diabody-type bispecific antibody.
Figure 5:
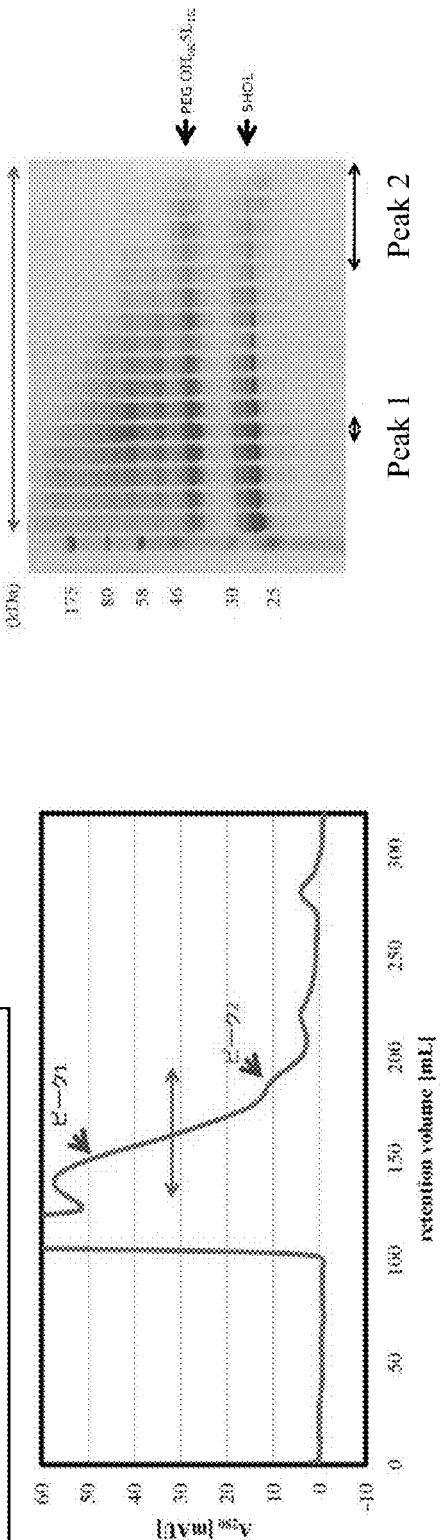

The same moles of the resulting PEG-modified single-chain polypeptide and the other single-chain polypeptide were then mixed, dialyzed for refolding and subjected to gel-filtration chromatography (Hiload superdex (trademark) 200 26/60 PG, flow rate:2 mL/min, eluate: PBS) for purification. Each fraction of retention volume of 120-200 mL was subjected to SDS-PAGE to give at peak 2 a fraction containing uniformly the diabody-type bispecific antibody according to the present invention (1 μM/mL), which comprised as a constituent the lysine-substituted light-chain variable region fragment of the 528 antibody wherein only Lys 108 of said light-chain variable region was site-specifically modified with PEG. These results are shown in FIG. 5.

EXAMPLE 6

Binding Activity of the PEG-modified Diabody-type Bispecific Antibody

The diabody-type bispecific antibody prepared in Example 5 was subjected to the flow cytometry described in Example 2. The lysine-substituted diabody-type bispecific antibody (100 pmol) obtained from the peaks 1 and 2 in the gel-filtration chromatography was used as a first antibody. However, the diabody-type bispecific antibody obtained from the peak 2 was reacted with T-LAK at an amount of 265 pmol. Ex (diabody-type bispecific antibody) wherein lysine residues had not been replaced was used instead of the first antibody for a positive control (referred to as "PC"). FITC-conjigate anti-HA antibody was then added as a detecting antibody and subjected to the detection of fluorescence.

Figure 6:
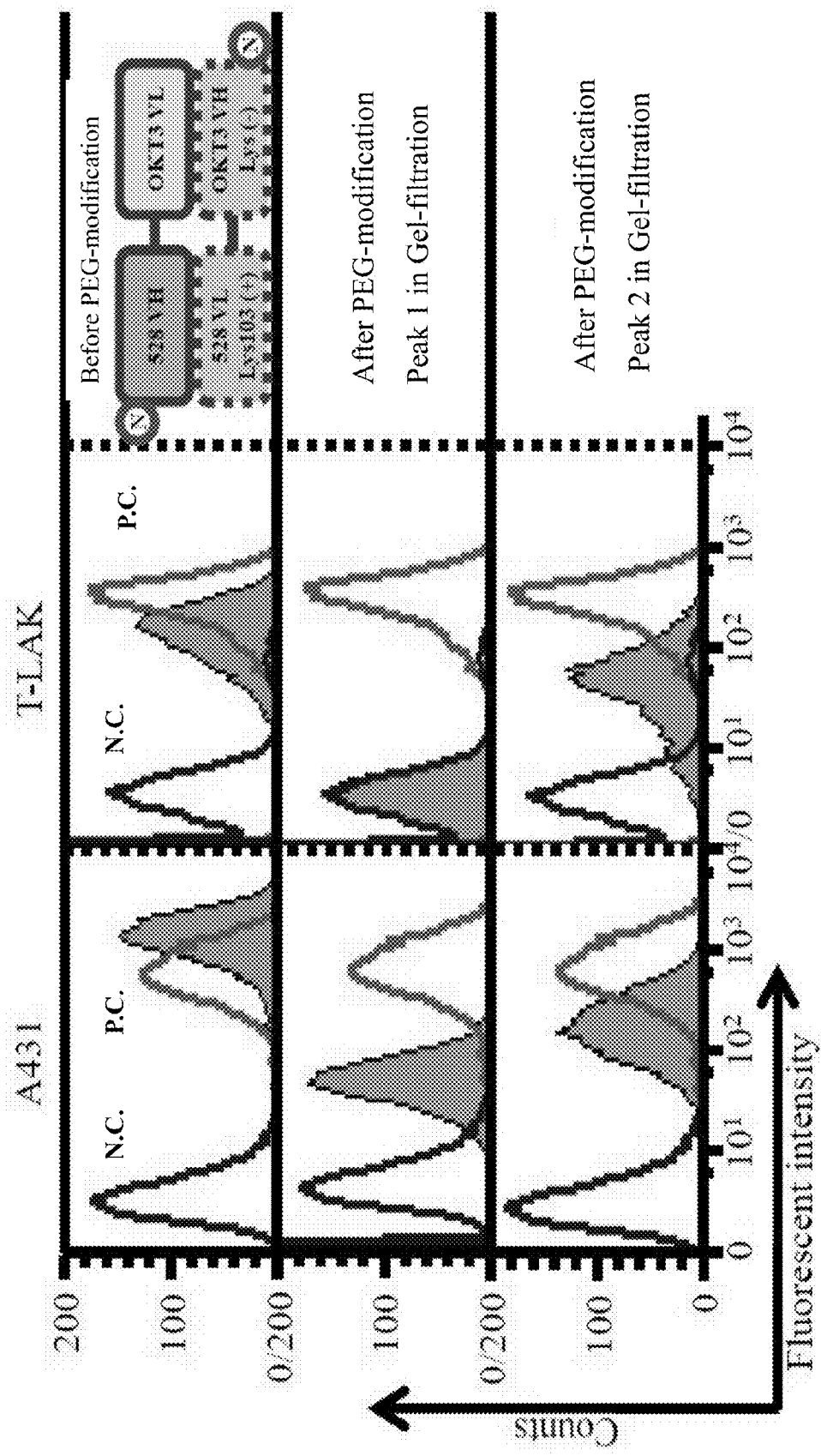
FIG. 6 shows the results of the binding activity of the PEG-modified humanized diabody-type bispecific antibody by means of a flow cytometry.

As a result, it was shown in FIG. 6 that the diabody-type bispecific antibody (100 pmol) obtained from the peak 2 in the gel-filtration chromatography had a binding activity for EGFR and CD3.

Industrial Applicability

The single-chain antibody would acquire polyvalent activity by being polymerized so as to show the growth-inhibiting activity (Patent Document 3). However, the distance between the variable regions could not optionally controlled. On the other hand, as the single-chain antibody according to the present invention comprises a single lysine residue as a reactive group at a particular site, chemical modification can be uniformly done and various high-functional structures could be designed depending on a chemical cross-linking agent with respect to said single-chain antibody. The single-chain antibody according to the present invention is therefore of a technologically superiority. For example, the polyvalent molecule may be prepared by using the cross-linking agent having a high branching number, and the single-chain antibody according to the present invention may be modified with anti-cancer agents, radioisotopes and the like to give the lysine-substituted antibody fragment targeting cancer-related antigens.

Furthermore, high-functionalization can be further developed by using the lysine-substituted humanized variable region fragment of the light-chain or heavy-chain of the anti-EGFR antibody or the single-chain antibody that is constructed from the fragment according to the present invention.

What is claimed:

1. A lysine-substituted humanized variable region fragment of a heavy-chain of an anti-human epithelial cell growth factor (EGF) receptor 1 (Her 1) antibody 528 (5H) that consists of the amino acid sequence of SEQ ID NO:4, wherein all of the lysine residues except for lysine (Lys) 19 in the 5H is replaced by other amino acids.

2. The lysine-substituted humanized variable region fragment of the heavy chain according to claim 1, which contains at least one of the following replacements in the 5H:

Lys 12 is replaced by Ala;
Lys 13 is replaced by Glu;
Lys 23 is replaced by Ala;
Lys 63 is replaced by Glu; or
Lys 65 is replaced by Gln.

3. The lysine-substituted humanized variable region fragment of the heavy chain according to claim 1, which contains the following replacements in the 5H:

Lys 12 is replaced by Ala;
Lys 13 is replaced by Glu;
Lys 23 is replaced by Ala;
Lys 63 is replaced by Glu; and
Lys 65 is replaced by Gln.

4. The lysine-substituted humanized variable region fragment of the heavy chain according to claim 1, wherein the one lysine residue or N-terminal amino acid is site-specifically modified.

5. The lysine-substituted humanized variable region fragment of the heavy-chain according to claim 4, wherein the one lysine residue or N-terminal amino acid is site-specifically modified with polyethylene glycol.

6. An antibody molecule comprising as a constituent the lysine-substituted humanized variable region fragment of the heavy chain according to claim 1.

7. The antibody molecule according to claim 6, which is selected from the group consisting of IgG-type antibody molecule, single-chain antibody (scFv), dimer of scFv, bispecific antibody, diabody-type bispecific antibody, highly functional bispecific antibody, and polymerized low-molecular antibody.

8. The dimer according to claim 7, wherein the one lysine residue contained in the lysine-substituted variable region fragment of a heavy chain is cross-linked.

9. A single-chain polypeptide constituting the antibody molecule of claim 6.

10. A method for the production of the antibody molecule of claim 6, comprising
culturing a host cell transformed with a vector, which is a co-expression vector containing a nucleic acid molecule encoding
a lysine-substituted humanized variable region fragment of a light-chain of an anti-human epithelial cell growth factor (EGF) receptor 1 (Her1) antibody 528 (5L) that consists of an amino acid sequence of SEQ ID NO:2, wherein all of the lysine residues, or all of the lysine residues except for one lysine residue at a particular site in the humanized variable region of the light chain is replaced by other amino acids and
a lysine-substituted humanized variable region fragment of a heavy-chain of an anti-human epithelial cell growth factor (EGF) receptor 1 (Her1) antibody 528 (5H) that consists of an amino acid sequence of SEQ ID NO:4, wherein all of the lysine residues except for lysine (Lys) 19 in the 5H is replaced by other amino acids
to express the two kinds of the single-chain polypeptides constituting said antibody molecule,
collecting and purifying said single-chain polypeptides, assembling the two kinds of the single-chain polypeptides, and separating and collecting the antibody molecule thus formed.

11. The method of claim 10 wherein the host cell is *E. coli*, and the two kinds of the single-chain polypeptides are collected from supernatant of a culture medium, periplasm fraction, intracellular soluble fraction or intracellular insoluble fraction.

12. A pharmaceutical composition comprising the antibody molecule of claim 6 as an active ingredient.

13. The pharmaceutical composition of claim 12 suitable for use in eliminating, hurting, damaging and/or reducing tumor cells.

* * * * *

SEQUENCE LISTING

```
<160> NUMBER OF SEQ ID NOS: 10

<210> SEQ ID NO 1
<211> LENGTH: 339
<212> TYPE: DNA
<213> ORGANISM: Artificial Sequence
<220> FEATURE:
<223> OTHER INFORMATION: Chimeric Sequence (h5L)
<220> FEATURE:
<221> NAME/KEY: CDS
<222> LOCATION: (1)..(339)

<400> SEQUENCE: 1 gat att gtg atg acc cag agc ccg ctg agc ctg ccg gtg acc cca ggc      48
Asp Ile Val Met Thr Gln Ser Pro Leu Ser Leu Pro Val Thr Pro Gly
1               5                   10                  15 gaa ccg gcg tcg att agc tgc cgc agc tcg cag aac atc gtg cat aat      96
Glu Pro Ala Ser Ile Ser Cys Arg Ser Ser Gln Asn Ile Val His Asn
            20                  25                  30 aac ggc att acc tat ctg gaa tgg tat ctg cag aaa ccg ggc caa agc     144
Asn Gly Ile Thr Tyr Leu Glu Trp Tyr Leu Gln Lys Pro Gly Gln Ser
        35                  40                  45 ccg cag ctg tta att tat aaa gtg agc gat cgc ttt agc ggc gtg ccg     192
Pro Gln Leu Leu Ile Tyr Lys Val Ser Asp Arg Phe Ser Gly Val Pro
    50                  55                  60 gat cgc ttt tcg ggc agc ggt agt ggc acc gat ttt acg ctg aaa att     240
Asp Arg Phe Ser Gly Ser Gly Ser Gly Thr Asp Phe Thr Leu Lys Ile
65                  70                  75                  80 agc cgc gtg gaa gcg gag gat gtt ggc gtg tat tac tgc ttt cag ggc     288
Ser Arg Val Glu Ala Glu Asp Val Gly Val Tyr Tyr Cys Phe Gln Gly
                85                  90                  95 agc cat atc ccg cca acc ttt ggc caa ggc acc aaa gtg gaa att aaa     336
Ser His Ile Pro Pro Thr Phe Gly Gln Gly Thr Lys Val Glu Ile Lys
                100                 105                 110 cgc                                                                 339
Arg

<210> SEQ ID NO 2
<211> LENGTH: 113
<212> TYPE: PRT
<213> ORGANISM: Artificial Sequence
<220> FEATURE:
<223> OTHER INFORMATION: Synthetic Construct: Chimeric Sequence (h5L)

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Asn
            20                  25                  30

Asn Gly Ile Thr Tyr Leu Glu Trp Tyr Leu Gln Lys Pro Gly Gln Ser
        35                  40                  45

Pro Gln Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

```
                      85                  90                  95

Ser His Ile Pro Pro Thr Phe Gly Gln Gly Thr Lys Val Glu Ile Lys
            100                 105                 110

Arg

<210> SEQ ID NO 3
<211> LENGTH: 354
<212> TYPE: DNA
<213> ORGANISM: Artificial Sequence
<220> FEATURE:
<223> OTHER INFORMATION: Chimeric Sequence (h5H)
<220> FEATURE:
<221> NAME/KEY: CDS
<222> LOCATION: (1)..(354)

<400> SEQUENCE: 3 cag gtg caa ctg gtt cag agc ggc gcg gaa gtg aaa aag ccg ggc gcg      48
Gln Val Gln Leu Val Gln Ser Gly Ala Glu Val Lys Lys Pro Gly Ala
1               5                  10                  15 tcg gtt aaa gtg agc tgc aaa gcc tca ggc tat acc ttt acg agc tac      96
Ser Val Lys Val Ser Cys Lys Ala Ser Gly Tyr Thr Phe Thr Ser Tyr
            20                  25                  30 tgg atg cat tgg gtg cgc cag gcc ccg ggt cag ggc ctg gaa tgg atg     144
Trp Met His Trp Val Arg Gln Ala Pro Gly Gln Gly Leu Glu Trp Met
        35                  40                  45 ggt aac att tat ccg ggc agc ggt ggc acc aac tat gcg gaa aaa ttt     192
Gly Asn Ile Tyr Pro Gly Ser Gly Gly Thr Asn Tyr Ala Glu Lys Phe
    50                  55                  60 aag aac cgc gtg acc atg acg cgt gat acc agc att tcg acg gcc tat     240
Lys Asn Arg Val Thr Met Thr Arg Asp Thr Ser Ile Ser Thr Ala Tyr
65                  70                  75                  80 atg gaa ctg agc cgc ctg cgt agc gat gac acc gcc gtg tat tac tgc     288
Met Glu Leu Ser Arg Leu Arg Ser Asp Asp Thr Ala Val Tyr Tyr Cys
                85                  90                  95 gcg cgc agt ggc ggt ccg tat ttt ttc gat tac tgg ggc cag ggt acg     336
Ala Arg Ser Gly Gly Pro Tyr Phe Phe Asp Tyr Trp Gly Gln Gly Thr
            100                 105                 110 ctg gtt acc gtg agc tcg                                             354
Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Synthetic Construct: Chimeric Sequence (h5H)

<400> SEQUENCE: 4

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Gly Thr Asn Tyr Ala Glu Lys Phe
    50                  55                  60

Lys Asn Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 5
<211> LENGTH: 321
<212> TYPE: DNA
<213> ORGANISM: Artificial Sequence
<220> FEATURE:
<223> OTHER INFORMATION: Chimeric Sequence (hOL)
<220> FEATURE:
<221> NAME/KEY: CDS
<222> LOCATION: (1)..(321)

<400> SEQUENCE: 5 gat atc cag atg acc cag agc ccg agc tct ctg agc gcg agc gtg ggc      48
Asp Ile Gln Met Thr Gln Ser Pro Ser Ser Leu Ser Ala Ser Val Gly
1               5                   10                  15 gat cgc gtg acc att acg tgc agc gcg tct agc tct gtg agc tat atg      96
Asp Arg Val Thr Ile Thr Cys Ser Ala Ser Ser Ser Val Ser Tyr Met
            20                  25                  30 aac tgg tac cag caa acc cca ggc aaa gcg ccg aaa cgc tgg att tat     144
Asn Trp Tyr Gln Gln Thr Pro Gly Lys Ala Pro Lys Arg Trp Ile Tyr
        35                  40                  45 gat acc agc aaa ctg gcg agc ggc gtg ccg agc cgc ttt agc ggc tct     192
Asp Thr Ser Lys Leu Ala Ser Gly Val Pro Ser Arg Phe Ser Gly Ser
    50                  55                  60 ggt agc ggc acc gat tat acg ttt acc att agc tct ctg cag ccg gaa     240
Gly Ser Gly Thr Asp Tyr Thr Phe Thr Ile Ser Ser Leu Gln Pro Glu
65                  70                  75                  80 gat att gcg acc tat tac tgc cag caa tgg agc tct aac ccg ttt acc     288
Asp Ile Ala Thr Tyr Tyr Cys Gln Gln Trp Ser Ser Asn Pro Phe Thr
                85                  90                  95 ttt ggc cag ggt acc aaa ctg cag att acc cgc                          321
Phe Gly Gln Gly Thr Lys Leu Gln Ile Thr Arg
            100                 105

<210> SEQ ID NO 6
<211> LENGTH: 107
<212> TYPE: PRT
<213> ORGANISM: Artificial Sequence
<220> FEATURE:
<223> OTHER INFORMATION: Synthetic Construct: Chimeric Sequence (hOL)

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105
```

```
<210> SEQ ID NO 7
<211> LENGTH: 357
<212> TYPE: DNA
<213> ORGANISM: Artificial Sequence
<220> FEATURE:
<223> OTHER INFORMATION: Chimeric Sequence (hOH)
<220> FEATURE:
<221> NAME/KEY: CDS
<222> LOCATION: (1)..(357)

<400> SEQUENCE: 7 cag gtg caa ctg gtg cag agc ggc ggt ggc gtt gtg cag ccg ggc cgc      48
Gln Val Gln Leu Val Gln Ser Gly Gly Gly Val Val Gln Pro Gly Arg
1               5                   10                  15 agc ctg cgc ctg tct tgc aaa gcg agc ggc tat acc ttt acg cgc tat      96
Ser Leu Arg Leu Ser Cys Lys Ala Ser Gly Tyr Thr Phe Thr Arg Tyr
            20                  25                  30 acc atg cat tgg gtg cgc cag gcg ccg ggc aaa ggt ctg gaa tgg att     144
Thr Met His Trp Val Arg Gln Ala Pro Gly Lys Gly Leu Glu Trp Ile
        35                  40                  45 ggc tat att aac ccg tct cgc ggc tat acc aac tat aat cag aaa gtg     192
Gly Tyr Ile Asn Pro Ser Arg Gly Tyr Thr Asn Tyr Asn Gln Lys Val
    50                  55                  60 aaa gat cgc ttt acc att agc cgc gat aac tct aaa aac acc gcg ttt     240
Lys Asp Arg Phe Thr Ile Ser Arg Asp Asn Ser Lys Asn Thr Ala Phe
65                  70                  75                  80 ctg cag atg gat agc ctg cgc ccg gaa gat acc ggc gtg tat ttt tgc     288
Leu Gln Met Asp Ser Leu Arg Pro Glu Asp Thr Gly Val Tyr Phe Cys
                85                  90                  95 gcg cgc tac tat gat gac cat tat agc ctg gat tat tgg ggc cag ggc     336
Ala Arg Tyr Tyr Asp Asp His Tyr Ser Leu Asp Tyr Trp Gly Gln Gly
            100                 105                 110 acc ccg gtg acc gtt agc tcg                                         357
Thr Pro Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct: Chimeric Sequence (hOH)

<400> SEQUENCE: 8

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115
```

<210> SEQ ID NO 9
<211> LENGTH: 798
<212> TYPE: DNA
<213> ORGANISM: Artificial Sequence
<220> FEATURE:
<223> OTHER INFORMATION: 528scFv
<220> FEATURE:
<221> NAME/KEY: CDS
<222> LOCATION: (1)..(798)

<400> SEQUENCE: 9

```
cag gtg caa ctg gtt cag agc ggc gcg gaa gtg aaa aag ccg ggc gcg      48
Gln Val Gln Leu Val Gln Ser Gly Ala Glu Val Lys Lys Pro Gly Ala
1               5                   10                  15 tcg gtt aaa gtg agc tgc aaa gcc tca ggc tat acc ttt acg agc tac      96
Ser Val Lys Val Ser Cys Lys Ala Ser Gly Tyr Thr Phe Thr Ser Tyr
            20                  25                  30 tgg atg cat tgg gtg cgc cag gcc ccg ggt cag ggc ctg gaa tgg atg     144
Trp Met His Trp Val Arg Gln Ala Pro Gly Gln Gly Leu Glu Trp Met
        35                  40                  45 ggt aac att tat ccg ggc agc ggt ggc acc aac tat gcg gaa aaa ttt     192
Gly Asn Ile Tyr Pro Gly Ser Gly Gly Thr Asn Tyr Ala Glu Lys Phe
    50                  55                  60 aag aac cgc gtg acc atg acg cgt gat acc agc att tcg acg gcc tat     240
Lys Asn Arg Val Thr Met Thr Arg Asp Thr Ser Ile Ser Thr Ala Tyr
65                  70                  75                  80 atg gaa ctg agc cgc ctg cgt agc gat gac acc gcc gtg tat tac tgc     288
Met Glu Leu Ser Arg Leu Arg Ser Asp Asp Thr Ala Val Tyr Tyr Cys
                85                  90                  95 gcg cgc agt ggc ggt ccg tat ttt ttc gat tac tgg ggc cag ggt acg     336
Ala Arg Ser Gly Gly Pro Tyr Phe Phe Asp Tyr Trp Gly Gln Gly Thr
            100                 105                 110 ctg gtt acc gtg agc tcg gcc ggc ggg ggc ggt tcg gat atc gtg atg     384
Leu Val Thr Val Ser Ser Ala Gly Gly Gly Gly Ser Asp Ile Val Met
        115                 120                 125 acc cag agc ccg ctg agc ctg ccg gtg acc cca ggc gaa ccg gcg tcg     432
Thr Gln Ser Pro Leu Ser Leu Pro Val Thr Pro Gly Glu Pro Ala Ser
    130                 135                 140 att agc tgc cgc agc tcg cag aac atc gtg cat aat aac ggc att acc     480
Ile Ser Cys Arg Ser Ser Gln Asn Ile Val His Asn Asn Gly Ile Thr
145                 150                 155                 160 tat ctg gaa tgg tat ctg cag aaa ccg ggc caa agc ccg cag ctg tta     528
Tyr Leu Glu Trp Tyr Leu Gln Lys Pro Gly Gln Ser Pro Gln Leu Leu
                165                 170                 175 att tat aaa gtg agc gat cgc ttt agc ggc gtg ccg gat cgc ttt tcg     576
Ile Tyr Lys Val Ser Asp Arg Phe Ser Gly Val Pro Asp Arg Phe Ser
            180                 185                 190 ggc agc ggt agt ggc acc gat ttt acg ctg aaa att agc cgc gtg gaa     624
Gly Ser Gly Ser Gly Thr Asp Phe Thr Leu Lys Ile Ser Arg Val Glu
        195                 200                 205 gcg gag gat gtt ggc gtg tat tac tgc ttt cag ggc agc cat atc ccg     672
Ala Glu Asp Val Gly Val Tyr Tyr Cys Phe Gln Gly Ser His Ile Pro
    210                 215                 220 cca acc ttt ggc cag ggc acc aaa gtg gaa att aaa cgc gcc gcg gct     720
Pro Thr Phe Gly Gln Gly Thr Lys Val Glu Ile Lys Arg Ala Ala Ala
225                 230                 235                 240 gca gaa caa aaa ctc atc tca gaa gag gat ctg aat cta ggg ggt ggc     768
Ala Glu Gln Lys Leu Ile Ser Glu Glu Asp Leu Asn Leu Gly Gly Gly
                245                 250                 255 atg cgc ggc tcg cac cat cat cac cac cat                              798
Met Arg Gly Ser His His His His His His
```

-continued

```
                    260                 265

<210> SEQ ID NO 10
<211> LENGTH: 266
<212> TYPE: PRT
<213> ORGANISM: Artificial Sequence
<220> FEATURE:
<223> OTHER INFORMATION: Synthetic Construct: 528scFv

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Gly Thr Asn Tyr Ala Glu Lys Phe
    50                  55                  60

Lys Asn Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser Ala Gly Gly Gly Gly Ser Asp Ile Val Met
        115                 120                 125

Thr Gln Ser Pro Leu Ser Leu Pro Val Thr Pro Gly Glu Pro Ala Ser
    130                 135                 140

Ile Ser Cys Arg Ser Ser Gln Asn Ile Val His Asn Asn Gly Ile Thr
145                 150                 155                 160

Tyr Leu Glu Trp Tyr Leu Gln Lys Pro Gly Gln Ser Pro Gln Leu Leu
                165                 170                 175

Ile Tyr Lys Val Ser Asp Arg Phe Ser Gly Val Pro Asp Arg Phe Ser
            180                 185                 190

Gly Ser Gly Ser Gly Thr Asp Phe Thr Leu Lys Ile Ser Arg Val Glu
        195                 200                 205

Ala Glu Asp Val Gly Val Tyr Tyr Cys Phe Gln Gly Ser His Ile Pro
    210                 215                 220

Pro Thr Phe Gly Gln Gly Thr Lys Val Glu Ile Lys Arg Ala Ala Ala
225                 230                 235                 240

Ala Glu Gln Lys Leu Ile Ser Glu Glu Asp Leu Asn Leu Gly Gly Gly
                245                 250                 255

Met Arg Gly Ser His His His His His His
                260                 265
```